(12) United States Patent
Spitz

(10) Patent No.: US 6,352,544 B1
(45) Date of Patent: Mar. 5, 2002

(54) APPARATUS AND METHODS FOR REMOVING VEINS

(76) Inventor: Gregory A. Spitz, 2000 Odgen Ave., Suite E101, Aurora, IL (US) 60504

( * ) Notice: Subject to any disclaimer, the term of this patent is extended or adjusted under 35 U.S.C. 154(b) by 0 days.

(21) Appl. No.: 09/510,227

(22) Filed: Feb. 22, 2000

(51) Int. Cl.[7] ............................................. A61B 17/22
(52) U.S. Cl. ..................................... 606/159; 606/190
(58) Field of Search ................................ 606/159, 192, 606/191, 194, 198, 1, 190

(56) References Cited

U.S. PATENT DOCUMENTS

| | | |
|---|---|---|
| 3,568,677 A | 3/1971 | Nolan et al. |
| 3,659,606 A | 5/1972 | Reimels |
| 3,741,214 A | 6/1973 | Tillander |
| 3,788,325 A | 1/1974 | Jacobsen |
| 3,943,225 A | 3/1976 | Koehn |
| RE31,873 E | 4/1985 | Howes |
| 4,528,982 A | 7/1985 | Wellenstam |
| 4,568,329 A | 2/1986 | Mahurkar |
| 4,583,968 A | 4/1986 | Mahurkar |
| 4,692,141 A | 9/1987 | Mahurkar |
| 5,011,489 A | 4/1991 | Salem |
| 5,047,013 A | 9/1991 | Rossdeutscher |
| 5,057,073 A | 10/1991 | Martin |
| 5,061,240 A | 10/1991 | Cherian |
| 5,087,265 A | 2/1992 | Summers |
| 5,373,840 A | 12/1994 | Knighton |
| 5,380,276 A | 1/1995 | Miller et al. |
| 5,395,384 A | 3/1995 | Duthoit |
| 5,486,159 A | 1/1996 | Mahurkar |
| 5,571,093 A | 11/1996 | Cruz et al. |
| 5,591,183 A | 1/1997 | Chin |
| 5,593,418 A * | 1/1997 | Mollenauer ............... 606/192 |
| 5,601,581 A | 2/1997 | Fogarty et al. |
| 5,601,589 A | 2/1997 | Fogarty et al. |
| 5,611,357 A | 3/1997 | Suval |
| 5,611,358 A | 3/1997 | Suval |
| 5,634,935 A | 6/1997 | Taheri |
| 5,758,665 A | 6/1998 | Suval |
| 5,776,111 A | 7/1998 | Tesio |
| 5,782,854 A | 7/1998 | Hermann |
| 5,792,168 A | 8/1998 | Suval |
| 5,795,326 A | 8/1998 | Siman |
| 5,797,947 A | 8/1998 | Mollenauer |
| 5,814,060 A | 9/1998 | Fogarty et al. |
| 5,817,013 A | 10/1998 | Ginn et al. |
| 5,843,072 A | 12/1998 | Furumoto et al. |
| 5,843,104 A | 12/1998 | Samuels |
| 5,893,858 A | 4/1999 | Spitz |
| 5,899,913 A | 5/1999 | Fogarty et al. |
| 5,902,316 A | 5/1999 | Mollenauer |
| 5,944,734 A | 8/1999 | Hermann et al. |

* cited by examiner

*Primary Examiner*—Kevin Truong
(74) *Attorney, Agent, or Firm*—Cardinal Law Group

(57) ABSTRACT

The present invention relates to devices and methods for removing veins in a venous system of a patient. One device for removing undesired veins includes an elongated member having first and second lumens extending longitudinally therein. The first lumen extends from the proximal end of the elongated member to a first opening at the distal end of the member. The second lumen extends from the proximal end of the elongated member to a second opening in the side of the elongated member. The proximal end of the elongated body is coupled to a connector having two separate tubes that communicate with the respective first and second lumen for the injection and removal of fluid. A vein attachment member, attached to the elongated member, is adapted to be secured to the vein. One method of removing undesired veins includes the steps of inserting a surgical instrument into a lumen of the vein, advancing the surgical instrument to a desired point along the vein, and attaching the distal end of the vein to the surgical instrument. The method also includes the steps extracting the surgical instrument to cause the vein to separate from its surrounding tissue, and supplying fluid through the instrument into the tissue where the vein has been extracted.

42 Claims, 2 Drawing Sheets

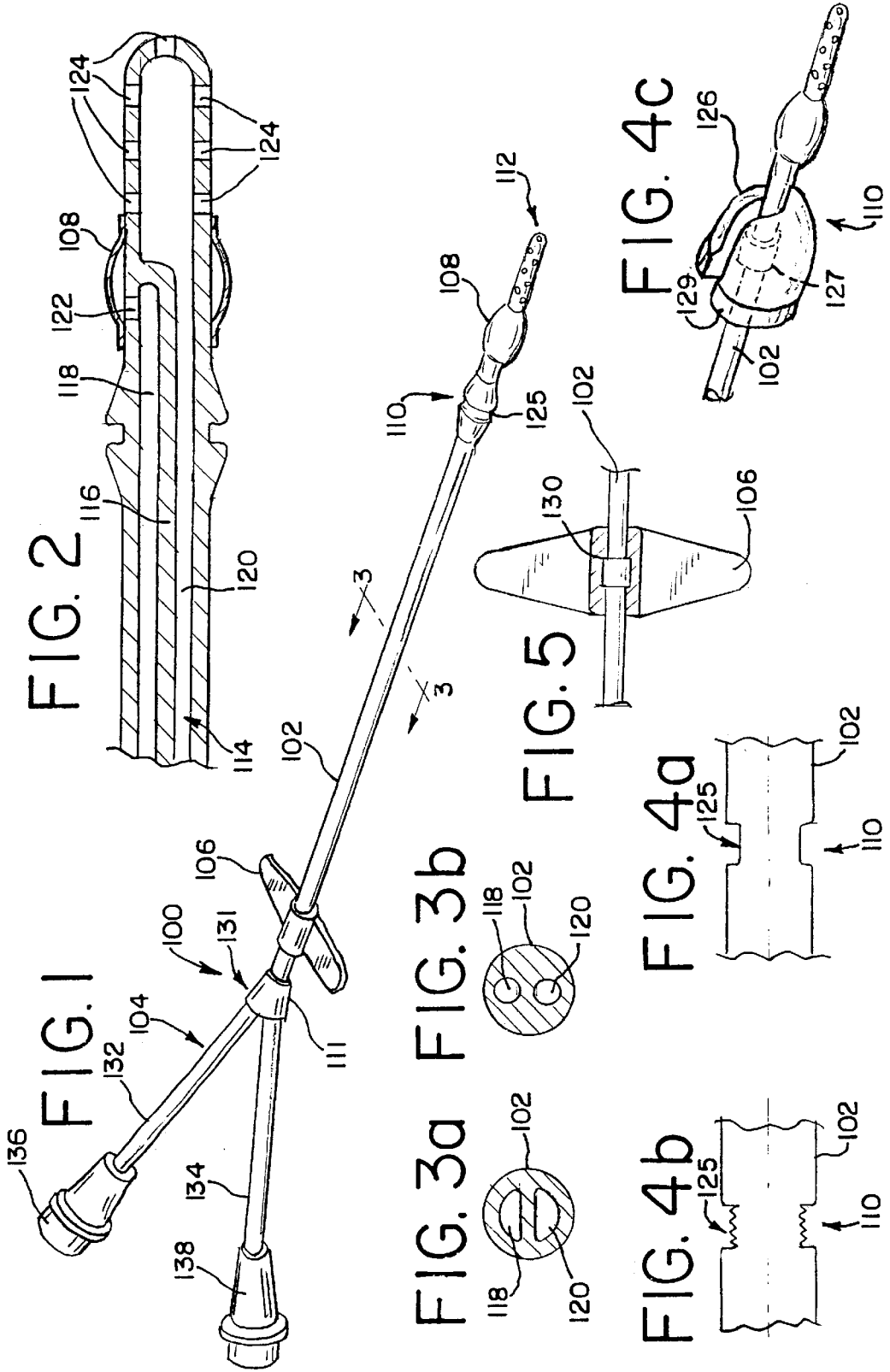

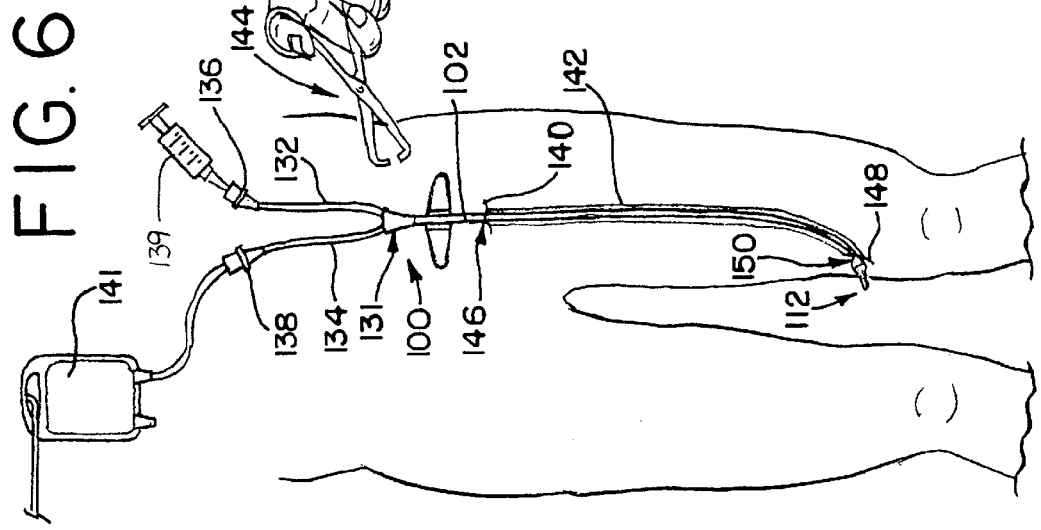

APPARATUS AND METHODS FOR REMOVING VEINS

FIELD OF THE INVENTION

The present invention relates generally to surgical apparatus and procedures. More particularly, it relates to methods and apparatus for stripping or removing veins, such as, varicose and saphenous veins, from a venous system of a patient.

BACKGROUND OF THE INVENTION

Varicose veins are typically found in the limbs of the lower portion of a human body. These veins have usually lost their ability to carry blood back to the heart and blood often accumulates in these veins. As a result, the veins may become swollen, distorted, dilated, elongated, and prominent.

A number of factors can contribute to the development of varicose veins, including heredity, obesity, posture, standing or sitting for a long periods of time, hormonal shifts, and excessive heat. Varicose veins may cause patients to experience various symptoms, such as aching, burning, swelling, cramping, and itching, while more serious complications of varicose veins can include thrombophlebitis, dermatitis, hemorrhage and ulcers. If these varicose veins are not treated, blood clots may form in the vein, and phlebitis or inflammation of the inside lining of the vein may occur. Even absent such symptoms, many patients seek medical treatment of varicose veins for cosmetic reasons.

Various approaches have been developed to treat varicose veins. In less complicated cases, elevation of the legs and use of support hosiery may be sufficient therapy to stop or slow the progression of the varicose veins. Alternatively, a technique called "sclerotherapy" may be used to treat varicose veins. In this procedure, the affected veins are injected with a sclerosing solution, such as sodium tetradecyl sulfate or pilocainol. Approximately one injection of the solution is usually administered for every inch of the affected veins, and multiple injections may be administered during a treatment session. The sclerosing solution causes subsequent inflammation and sclerosis of the veins. The sclerosis results in localized scarring or closure of the veins, which forces rerouting of the blood away from the affected veins.

However, patients usually have to undergo two or more sclerotherapy treatments in order to alleviate the varicose veins to a satisfactory degree. Other fine reddish blood vessels may also appear around the treated area, requiring further injections. Nevertheless, the sclerotherapy technique may not be a permanent or complete solution since the condition of the varicose veins may reoccur within five years.

Sclerotherapy may also have other potential complications, including browning splotches or bruising of the skin, formation of blood clots in the veins, inflammation, adverse allergic reactions, ulceration, phlebitis, anaphylactic overdose, ischemia, skin or fat necrosis, and peripheral neuropathy. Furthermore, sclerotherapy cannot be applied to the saphenous vein in the upper thigh region due to the risk of sclerosis of the deep veins. Thus, the sclerotherapy technique is often combined with an operative procedure, such as ligation of a portion of the saphenous vein.

Another technique to treat varicose veins is called stab avulsion phelbectomy with hooks. In this technique, one or more incisions are made in the skin of a patient, and a hook is inserted into the incision to grip or hook the veins to be removed. When the veins are grabbed, the veins are pulled though the surgical incision and severed. However, this procedure usually requires two surgeons to perform the procedure and takes about 2–3 hours. In addition, this procedure usually requires multiple incisions in the patient in order to hook the affected veins. Furthermore, it is often difficult to completely remove the entire affected veins using this procedure.

Varicose veins can also be removed by a procedure commonly referred to as "stripping." To remove a saphenous vein using a traditional stripping procedure, a large incision is made near the groin area of a patient and the saphenous vein is separated from the femoral vein. The saphenous vein is also usually dissected near the lower portion of the leg. Multiple large incisions are made along the leg in order to sever and ligate the tributary veins of the saphenous vein. A vein stripper, such as a wire, is then inserted into the lumen of the saphenous vein. The wire is then advanced through the saphenous vein and tied to the lower end of the vein. The wire is then removed top through the groin incision to extract the vein. After the saphenous vein is completely removed from the leg, the large incisions along the leg are closed.

However, this striping procedure is usually painful and often requires overnight hospitalization. In addition, numerous incisions are usually required to remove the saphenous vein and often leave permanent unsightly scars along the leg of a patient. Additionally, the large incisions create a risk of infection to the patient and may not heal properly, especially patients who have poor circulation in their extremities. There are also associated complications with this technique, such as, for example, blood loss, pain, infection, hematoma, nerve injury, and swelling.

SUMMARY OF THE INVENTION

In view of the above, the present invention provides methods and apparatus for stripping or removing undesired veins, such as, varicose and saphenous veins, in a venous system of a patient. The apparatus and methods of the present invention provide an efficient and minimally intrusive procedure to remove the undesired veins. The apparatus further allows a surgeon to introduce fluid, such as saline mixed with a local anesthetic, to irrigate the tissue where the vein has been extracted during the surgical procedure. The apparatus and procedures of the present invention also allows the undesired veins to be completely removed with minimal scarring.

One method of removing undesired veins in accordance with the present invention includes the steps of inserting a surgical instrument into a lumen of the vein, advancing the surgical instrument to a desired point along the vein, and attaching the distal end of the vein to the surgical instrument. The method also includes the steps of extracting the surgical instrument to cause the vein to separate from its surrounding tissue, and supplying fluid through the instrument into the tissue where the vein has been extracted.

One surgical apparatus for removing undesired veins in accordance with the present invention includes an elongated member having first and second lumens extending longitudinally therein. The first lumen extends from the proximal end of the elongated member to a first opening at the distal end of the elongated member. The first opening permits fluid to be introduced into the tissue where the vein has been extracted. The second lumen extends from the proximal end of the elongated member to a second opening in the side of the elongated member. The proximal end of the elongated body is coupled to a connector having two separate tubes that communicate with the respective first and second lumen for the injection and removal of fluid. A vein attachment member, attached to the elongated member, is adapted to be secured to the vein.

The invention, together with further attendant advantages, will best be understood by reference to the following detailed description of the presently preferred embodiments of the invention, taken in conjunction with the accompanying drawings. It is to be understood that both the foregoing general description and the following detailed description are exemplary and explanatory and are intended to provide further explanation of the invention as claimed.

BRIEF DESCRIPTION OF THE DRAWINGS

FIG. 1 is a perspective view of a surgical apparatus to remove undesired veins in a venous system of a patient;

FIG. 2 is a fragmentary cross-sectional side view of a distal portion of the surgical apparatus of FIG. 1;

FIG. 3a is a cross-sectional view taken about line 3–3 of FIG. 1;

FIG. 3b is another cross-sectional view taken about line 3–3 of FIG. 1;

FIG. 4a is a fragmentary side view illustrating another embodiment of a vein attachment section of the surgical apparatus of FIG. 1;

FIG. 4b is a fragmentary side view illustrating another embodiment of a vein attachment section of the surgical apparatus of FIG. 1;

FIG. 4c is a fragmentary side view illustrating another embodiment of the vein attachment section of the surgical apparatus of FIG. 1;

FIG. 5 is a fragmentary partial cross-sectional side view illustrating a handle of the surgical apparatus of FIG. 1;

FIG. 6 is a diagrammatical view of a vein being removed from a patient by the surgical apparatus of FIG. 1;

FIG. 7 is a side elevational view of another embodiment of a surgical apparatus to remove undesired veins in a venous system of a patient;

FIG. 8 is a side elevational view of another embodiment of a surgical apparatus to remove undesired veins in a venous system of a patient; and FIG. 9 is a side elevational view of another embodiment of a surgical apparatus to remove undesired veins in a venous system of a patient.

DETAILED DESCRIPTION OF THE PRESENTLY PREFERRED EMBODIMENTS

Before explaining the preferred embodiments in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the preferred embodiments of the present invention for the convenience of the reader and are not for the purpose of limitation. Similar reference numbers refer to similar parts throughout the drawings.

Referring now to the drawings in detail, and particularly to FIG. 1, a preferred is embodiment of a surgical apparatus or vein stripper 100 to remove undesired veins, such as varicose and saphenous veins, in a venous system of a patient is illustrated. The surgical apparatus 100 allows a surgeon to introduce fluid, such as saline mixed with local anesthetic, to irrigate the tissue where the vein has been extracted during the surgical procedure. The saline induces blood clotting, reduces bleeding, and decreases the pain to the patient during the vein removal procedure. The surgical apparatus 100 further allows undesired veins to be completely removed with minimal scarring.

The surgical apparatus 100 is preferably a disposable unit to eliminate resterilization of the portions of the apparatus that enter into the patient's body. As shown in FIG. 1, the surgical apparatus 100 generally includes an elongated member or body 102, a connector assembly 104, a handle 106, an inflatable/deflatable balloon 108, and a vein attachment section 110.

The proximal end of the elongated body 102 is attached to the distal end 111 of the connector assembly 104, and the distal end of the elongated body 102 preferably has a rounded bullet-shaped tip 112 which facilitates cannulation or insertion of the elongated body 102 into a lumen of a vein. It will be recognized that the distal end of the elongated body can have any suitable shape (i.e., conical) and size. The distal end 112 of the elongated body may also include a light source to allow the surgeon to view the area near thereto.

The elongated body 102 preferably has an outer diameter slightly smaller than the inner diameter of the vein to be removed or extracted. The elongated body 102 preferably has a substantially circular cross-section, but may have any suitable cross-section, such as a square or an elliptical cross-section. The outer surface of the elongated member 102 can be coated with a polyeetrafluoroethylne, silicone, or other low friction coating to provide lubricity and ease of movement of the surgical apparatus 100 during use.

The elongated body 102 of the surgical apparatus 100 can be constructed of any suitable material which provides sufficiently rigidity to permit insertion of the elongated body 102 into the vein and sufficiently flexibility to permit navigation of the elongated body 102 through the lumen of the vein. The elongated body 102 can be constructed from nylon, Teflon, polyurethane, or polyethylene. It will be recognized that the elongated body 102 can be made from a variety of other materials including, for example, polypropylene, polyamide, polyethylenterephthalate, polyamide, other polymers and polycarbonates as well as other suitable forms of plastic. The elongated member 102 can have any suitable length depending upon the application and the particular surgical procedure.

A reinforcing strip or member (not shown) may be embedded along substantially the entire length of the elongated body 102 of the surgical apparatus 100. The reinforced strip can be substantially stiff to permit the elongated body 102 to be advanced through the lumen of the vein. The reinforced strip can be made of any suitable material, such as nylon, plastic or the like.

As shown in FIG. 2, the elongated body 102 of the surgical apparatus 100 further has an interior cavity or conduit 114 positioned therein and extending axially from its proximal end. The cavity 114 can have any suitable size and shape. The elongated body 102 preferably has an internal divider 116 extending axially from the proximal end of the elongated body 102 to a point near its distal end. The divider 116 divides the interior cavity 114 into a first lumen or passageway 118 and a second lumen or passageway 120 within the interior of the elongated body 102. The lumens 118 and 120 can have semicircular or "D" traverse cross sections (see FIG. 3a), circular cross sections (see FIG. 3b), or any other suitable cross sectional shape. It will be recognized the elongated body 102 can have any suitable number of lumens or passageways. It will also be recognized that the elongated body 102 may include a fiber optic visualization apparatus to allow the surgeon to observe the area adjacent to the distal end of the elongated body 102.

The first and second lumens 118 and 120 of the elongated body 102 are independent from and are not communicative with one another. The first lumen 118 extends longitudinally from the proximate end of the elongated body 102 to one or more openings or apertures 122 (one being shown) near the distal end of the elongated body 102. Preferably, the opening 122 is in the side wall of the elongated body 102 and is generally cylindrically shaped. The opening 122 permits fluid to be transmitted from the first lumen 118 into the interior of the balloon 108 to controllably inflate and/or deflate the balloon 108 as further described below.

The second lumen 120 of the elongated body 102 extends longitudinally from the proximate end of the elongated body 102 to one or more openings or apertures 124 near the distal end of the elongated body 120. The openings 124 are preferably in the side wall of the elongated body 102. The openings 124 are preferably cylindrical shaped, but may be any suitable shape. The openings 124 allow fluid to be transmitted from the second lumen 120 into the tissue where the vein has been extracted during the vein removal procedure as further described below. The fluid induces blood clotting, reduces bleeding, and decreases pain to the patient during the vein removal procedure.

As shown in FIG. 1, the balloon 108 of the surgical apparatus 100 is attached near the distal end of the elongated body 102. The balloon 108 can be made of latex, silicone rubber, polyethylene, polyamide or any other suitable material. The balloon is preferably reinforced with metal or other suitable material. The balloon 108 can be inflated as the elongated body 102 is being advanced through the lumen of the vein to expand constricted areas of the vein and to indicated to the surgeon where the distal end of the elongated body 102 is located. The balloon 108 can be configured in various sizes and many different shapes, including, but not limited to, rectangular, conical, elliptical, cylindrical, and the like.

The balloon 108 is preferably disposed over the opening 122 in the elongated body 102 to permit the first lumen 118 to be in fluid communication with the interior of the balloon 108. As a result, when fluid is transmitted through the opening 122 and into the interior of the balloon 108, the fluid will cause the balloon 108 to inflate. When the fluid is extracted or removed from the interior of the balloon 108, the balloon 108 will deflate. The fluid that may be used to inflate and deflate the balloon 108 can be a liquid such as water or saline, or a gas such as air, $CO_2$, inert gas, carbon dioxide, helium, nitrogen, or the like. The fluid may be injected into and removed from the first lumen 118 of the surgical apparatus 100 by a fluid source such as, for example, a rubber bulb, a syringe, a micro pump or the like.

As shown in FIG. 1, the vein attachment section 110 of the surgical apparatus 100 is disposed near the distal end of the elongated body 102. The vein attachment section 110 allows a surgeon to fasten or secure the severed distal end of the vein to the elongated body 102. To attach the vein to the elongated body 102, the distal end of the vein is preferably disposed over the vein attachment section 110 and attached to or compressed against the vein attachment section 110 by a clip, a suture, thread or the like. Once the vein is fastened to the vein attachment section 110, the surgeon begins to pull or retract the elongated body 102 from the patient to extract the vein from the surrounding tissue.

The vein attachment section 110 preferably has a generally spherical or cylindrical body having a circumferential groove or slot 125 to permit a vein to be compressed therein. It will be recognized that the vein attachment section 110 may have a variety of configurations. For example, as shown in FIG. 4a, the vein attachment section 110 may include circumferential groove or slot 125 defined in the outer surface or side wall of the elongated body 102. As shown in FIG. 4b, the vein attachment section may include a circumferential groove 125 having circumferential serrations or teeth, which can be either parallel or may be disposed as a spiral, such as threads. The vein can be attached by a suture or thread to compress the vein into the circumferential groove and/or the serrations to prevent slippage so that the vein follows the elongated body 102 when the vein is being extracted. It will be recognized that the circumferential groove 125 of FIG. 4b can be defined in the outer surface of the elongated body or can be defined in a generally spherical body attached to the elongated body 102 as shown in FIG. 4a.

Another embodiment of the vein attachment section 110 is illustrated as shown in FIG. 4c. The vein attachment section 110 includes a stripper head 126 that can be detachably coupled to an enlarged section 127 of the elongated body 102. The stripper head 126 can be can be acorn shaped but can have various shapes and sizes to accommodated different vein sizes. The stripper head 126 can be constructed of plastic or nylon, but may be manufactured from any suitable material. The stripping head 126 has a blunt or serrated edge 129 that is adapted to remove the vein during the stripping operation.

As shown in FIG. 4c, the elongated body 102 of the surgical apparatus 100 is preferably received in a radial slot of the striper head 126. Thereafter, the stripper head 126 is locked in an aligned position by displacing the elongated body 102 and the stripper head 126 in relation to each other in such a manner that an enlarged section 127 is received in the recess or bore defined in an end surface of the stripper head 126. As the surgeon removes the elongated body 102 from the body of the patient, the stripper head 126 strips or severs the vein from the tissue surrounding the outer wall of the vein.

Referring again to FIG. 1, the handle 106 of the surgical apparatus 100 is disposed near the proximal end of the elongated body 102. The handle 106 can be detachably or permanently coupled to the elongated body. The handle 106 can be made of any suitable material, such as nylon, plastic or the like. One embodiment of a handle 106 that is detachable from the elongated body is illustrated in FIG. 5. The elongated body 102 is preferably received in a radial slot of the handle 106. Thereafter, the handle 106 can be locked in an aligned position by displacing the elongated body 102 and the handle 106 in relation to each other in such a manner that an enlarged section 130 of the elongated body 102 is received in the recess or bore defined in an end surface of the handle 106.

As shown in FIG. 1, the proximal end of the elongated body 102 is attached to the distal end 111 of the connector assembly 104 of the surgical apparatus 100. The connector assembly 104 includes a branch connector or a hub 131 and one or more extension tubes 132 and 134 (two being shown). The hub 131 connects the proximal portions of the first and second lumens 118 and 120 of the elongated body 102 to respective fluid inlet lines of the extension tubes 132 and 134. The extension tubes 132 and 134 are relatively soft and flexible so that they can be easily manipulated by a surgeon. In addition, clamps or stop cocks (not shown) may also be attached to the extension tubes to regulate or interrupt the flow of fluid through the lumens of the extension tubes 132 and 134.

The proximal ends of the extension tubes 132 and 134 are attached to connectors or adapters 136 and 138, respectively. The connectors 136 and 138 can include, but are not limited to, Luer Lock connectors, quick connect fittings, ferrule connectors, threadable connectors, and the like. The connectors 136 and 138 permit the extension tubes 132 and 134 to be attached or coupled to other devices such as, fluid sources. For example, a hand-operated syringe 139 (see FIG. 6) can be coupled to the connector 136 for transmitting a suitable fluid through the first lumen 118 of the elongated body 102 to permit inflation and deflation of the balloon. A saline bag 141 (see FIG. 6) can also be coupled to the connector 138 for transmitting a suitable fluid through the second lumen 120 of the elongated body 102 and into the tissue where the vein has been extracted.

Referring now to FIG. 6, the method of using the surgical apparatus 100 to remove or strip undesired veins, such as varicose and saphenous veins, of a patient will now be described. Although the method will be described in reference to a vein in a patient's leg, it will be recognized that the following method can be used to strip any suitable vein. During this procedure, the patient may undergo a general anesthetic, regional anesthetic (i.e., spinal or epidural), or a local anesthetic.

As shown in FIG. 6, the surgeon effects an entrance into the patient by cutting a first incision 140 through the layer of skin in the patient's leg over an undesired vein 142. The first incision 140 may be made by a blade, such as a mall surgical scalpel, such as a no. 67 scalpel blade. After the first incision 140 is made, the surgeon inserts a surgical instrument 144, such as a ring clamp, into the first incision 140 and grasps the vein. The surgeon then servers or divides the vein 142 to provide a first free end 146. The distal end of the elongated body 102 of the surgical apparatus 100 is inserted through the first incision 140 and into the lumen of the vein 142. The elongated body 102 is advanced or navigated with the balloon 108 deflated through the lumen of the vein 142. As the distal end of the elongated body 102 is being advanced, the surgeon can inflate the balloon 108 to determine where the distal end of elongated body 102 is located. The surgeon may also inflate the balloon 108 to expand constricted areas of the vein 142. As the elongated body 102 is being advanced through the vein, fluid may be transmitted from the distal portion of the elongated body 102 to dilute and/or hydrodissect the vein 142. For example, anesthesia can be introduced into the lumen of the vein to ensure postoperative comfort and reduce hematoma or bleeding.

After the distal end of the elongated body 102 is guided along the vein to a desired position, the surgeon makes a second incision 148 through the layer of skin in the patient's leg near the distal end of the elongated body 102. Once the second incision 148 is made, the surgeon introduces the surgical instrument 144, such as a ring clamp, into the second incision 148 and grasps the vein 142 with a surgical instrument 100. The surgeon then servers the vein 142 to provide a second free end 150.

The second free end 150 is attached to the vein attachment section 110 by a suture, thread, clip, or the like. The balloon 108 is then inflated with 1.5–2.0 ml of fluid. As the surgical instrument 100 is removed from the patient, the vein wall is folded back on itself, so that the outer surface of the vein travels downward with the vein lumen and becomes an inner surface. The venous tissue thus peels away from the surrounding tissue, minimizing trauma to the patient. Vein branches are usually torn off as the vein is pulled by the surgical apparatus 100. As the vein is being extracted, fluid is transmitted under pressure from the distal portion of the elongated body 102 into the cavity formed where the vein is extracted from the surrounding tissue. Preferably, the fluid is transmitted under 4–500 mmHg pressure to ensure postoperative comfort and decrease bleeding and hematoma formation. The fluid preferably includes 50 cc of 1% Lidocaine, 2 cc of 1:1000 epinephrine (adrenaline), and 1 Liter of Saline.

In the case where the vein attachment section 110 has a detachable stripping head 126 (see FIG. 4c), the surgeon preferably attaches the stripping head on the end of the elongated body 102 once it emerges from the second free end 150 of the vein 142. The vein is then extracted by pulling the handle causing the stripper head 126 to strip or sever the vein from the surrounding tissue. Vein branches are usually torn off by the stripper head 126 as the vein is pulled by the surgical apparatus 100. As the vein is being extracted, fluid is transmitted under pressure from the distal end of the elongated body 102 into the cavity formed where the vein is extracted from the surrounding tissue.

After the vein has been removed, the first and second incisions 140 and 148 can be closed with steri-strips or any suitable closure material. Although these incisions can be closed with sutures, it is considered unnecessary due to the small size of the incisions, and is also undesirable since suturing the skin can cause scarring.

Referring now to FIG. 7, another embodiment of a surgical apparatus 200 to remove undesired veins is illustrated. The surgical apparatus 200 in many respects corresponds in construction and function to the previously described surgical instrument 100 of FIG. 1. Components of the surgical instrument 200 of FIG. 7 which generally correspond to those components of the surgical instrument 100 of FIG. 1 are designated by like reference numerals in the two-hundred series. As shown in FIG. 7, the surgical instrument 200 includes a connector member 204 having one extension tube 232 and an elongated body 202 without an inflatable/deflatable balloon.

Referring now to FIG. 8, another embodiment of a surgical instrument 300 to remove undesired veins is illustrated which in many respects corresponds in construction and function to the previously described surgical instrument 100 of FIG. 1. Components of the surgical instrument 300 of FIG. 8 which generally correspond to those components of the surgical instrument 100 of FIG. 1 are designated by like reference numbers in the three-hundred series. As shown in FIG. 8, the surgical apparatus 300 includes a connector member 304 having one extension tube 332 and an elongated body 302 without openings at its distal end.

Referring now to FIG. 9, another surgical system 400 is illustrated which in many respects corresponds in construction and function to the previously described surgical system 100 of FIG. 1. Components of the surgical system 400 of FIG. 9 which generally correspond to those components of the surgical instrument 100 of FIG. 1 are designated by like reference numbers in the four-hundred series. The surgical apparatus 400 includes an elongated body 402 having a detachable distal portion 450. Preferably, the elongated body 402 has a threaded member 452 that mates with an internally threaded axial bore 454 formed in detachable distal end portion 450. Although the surgical apparatus 400 is shown with a connector member 404 having one extension tube 432 and an elongated body 402 without a balloon, the connector member 404 can have any suitable number of extension tubes and can have a balloon.

The apparatus and methods of the present invention allow a surgeon to efficiently remove undesired veins from a body of a patient. For example, a saphenous vein of a patient can be removed using the surgical apparatus described herein. The surgical apparatus allows the surgeon to introduce fluid, such as saline, into the tissue where the vein has been extracted during the surgical procedure. The saline induces blood clotting, reduces bleeding, and decreases the pain to the patient during the vein removal procedure. The surgical apparatus can further allow undesired veins to be completely remove with minimal scarring.

Although the present invention has been described in detail by way of illustration and example, it should be understood that a wide range of changes and modifications can be made to the preferred embodiments described above without departing in any way from the scope and spirit of the invention. For example, a fiber optic visualization apparatus can be incorporated into any of the surgical apparatus described above.

Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

I claim:

1. A method for stripping an undesired vein from a human body comprising the steps of:
    making a first incision through a skin layer of a patient in close proximity to the undesired vein;
    severing the vein at a first site to provide a first end of the vein;
    inserting an elongated body of a surgical apparatus into the vein;
    advancing a distal end of the elongated body through the vein to a desired position;
    making a second incision through the skin layer of a patient in close proximity to the distal end of the elongated body;
    severing the vein at a second site to provide a second end of the vein;
    attaching the second end of the vein to the elongated body;
    retracting the elongated body to separate the vein from the tissue surrounding the vein;
    while the vein is being separated from the surrounding tissue, injecting fluid through an aperture near the distal end of the elongated body into the surrounding tissue where the vein has been extracted to reduce bleeding; and
    discarding the vein without reuse.

2. The method of claim 1 further comprising the step of closing one of the first and second incisions.

3. The method of claim 1 further comprising the steps of retracting the elongated body from the patient by pulling on a handle attached near a proximal end of the elongated body.

4. The method of claim 1 further comprising the step of inflating a balloon.

5. The method of claim 4 wherein the balloon is inflating by transmitting fluid through a lumen of the elongate body and into the interior of the balloon.

6. The method of claim 1 wherein the vein is a saphenous vein.

7. The method of claim 4 wherein the balloon is inflated when the distal end has reached the desired position and remains inflated while the vein is being extracted.

8. The method of claim 1 wherein the first incision is made near the groin of a patient.

9. The method of claim 1 further comprising the step of repeating said injecting step while the vein is being extracted.

10. The method of claim 1 wherein the second end of the vein is attaching to a vein attachment member of the surgical apparatus.

11. The method of claim 10 wherein the vein attachment member includes a circumferential groove.

12. The method of claim 10 wherein the vein attachment member is detachably coupled to the elongated body.

13. The method of claim 1 further comprising the step of injecting fluid into the vein while the elongated body is being advanced through the vein.

14. The method of claim 1 wherein the vein is attached to the elongated body by a suture.

15. The method of claim 1 where fluid is transmitted through a lumen of the elongated body and through at least one opening near the distal end of the elongated body.

16. The method of claim 1 wherein the retracting step includes the step of turning the vein inside out.

17. The method of claim 1 wherein the fluid is pressurized above 200 mmHG.

18. The method of claim of 1, wherein the fluid comprises a non-vasodilator fluid.

19. A method of using a surgical instrument to remove a vein from a human body comprising the steps of:
    inserting the surgical instrument into a lumen of the vein;
    advancing the surgical instrument to a desired point along the vein;
    attaching a distal end of the vein to the surgical instrument;
    extracting the surgical instrument to cause the vein to separate from the tissue surrounding the vein;
    while the vein is being separated from the surrounding tissue, supplying fluid through the instrument into the surrounding tissue where the vein has been extracted to reduce bleeding; and
    discarding the vein without reuse.

20. The method of claim 19 further comprising the step of attaching the vein to a vein attachment member of the surgical instrument.

21. The method of claim 19 wherein the extracting step includes the step of turning the vein inside out.

22. The method of claim 19 wherein the fluid is pressurized above 200 mmHG.

23. A method of using a surgical instrument to remove a vein from a human body comprising the steps of:
    inserting the surgical instrument into a lumen of the vein;
    advancing the surgical instrument to a desired point along the vein;
    attaching a stripping head to the surgical instrument;
    extracting the surgical instrument to cause the stripper head to separate the vein from its surrounding tissue;
    while the vein is being separated from the surrounding tissue, supplying fluid through the instrument into the surrounding tissue where the vein has been removed therefrom; and discarding the vein without reuse.

24. The method of claim 23 wherein the retracting step include the step of turning the vein inside out.

25. The method of claim 23 wherein the fluid is pressurized above 200 mmHG.

26. A surgical apparatus to remove an undesired vein from a body of a patient without reuse of the vein comprising:

an elongated member having a proximal portion and a distal portion, the distal portion of the elongated member sized for insertion into a lumen of a vein and having at least one aperture;

at least one longitudinal lumen extending substantially along the length of the elongated member and in fluid communication with the at least one aperture to permit fluid to be introduced into tissue where the vein has been extracted to reduce bleeding; and a vein attachment member, coupled to the elongated member, to permit the vein to be secured thereto and to allow the vein to be extracted from the body of the patient when the elongated member is being retracted.

27. The surgical apparatus of claim 26 wherein the vein attachment member includes a circumferential grove to permit the vein to be secured thereto by one of a suture, thread, and clip.

28. The surgical apparatus of claim 26 wherein the vein attachment member is detachably coupled to the elongated member.

29. The surgical apparatus of claim 26 wherein the at least one lumen is in fluid communication a fluid conveying device.

30. The surgical apparatus of claim 29 wherein the fluid conveying device includes one a syringe and fluid bag.

31. The surgical apparatus of claim 26 further comprising a second lumen extending axially along the length of the elongated member and in fluid communication with a second opening near the distal portion.

32. The surgical apparatus of claim 31 further comprising a balloon attached to the distal portion of the elongated member, the balloon being inflatable when fluid is introduced through the second opening.

33. The surgical apparatus of claim 31 further comprising a fluid source in fluid communication with the second lumen for inflating and deflating the balloon by controlled transmission of fluid pressure.

34. The surgical apparatus of claim 26 further comprising visualization means for illumination and visualization of a region adjacent to the distal end of the elongated member.

35. The surgical apparatus of claim 26 wherein the vein is turned inside during extraction.

36. The surgical apparatus of claim 26 wherein the fluid is pressurized above 200 mmHG.

37. A surgical instrument for removing a vein without reuse comprising:

an elongated member having first and second lumens extending longitudinally therein, the first lumen extending from a proximal end of the member to a first opening near a distal end of the member, and the second lumen extending from the proximal end of the member to a second opening in the side of the surface of the elongated tube, the first opening capable of introducing fluid into the tissue where the vein has been extracted;

the proximal end of the elongated member coupled to a connector having two separate tubes communicating with the respective first and second lumens for the injection and removal of fluid from the tissue where the vein has been removed; and a vein attachment member, attached to the elongated member, adapted to be secured to the vein.

38. The surgical apparatus of claim 37 wherein the vein is turned inside during extraction.

39. The surgical apparatus of claim 37 wherein the fluid is pressurized above 200 mmHG.

40. A surgical instrument for removing a vein without reuse comprising:

an elongated member having first and second lumens extending longitudinally therein, the first lumen extending from a proximal end of the member to a first opening near a distal end of the member, and the second lumen extending from the proximal end of the member to a second opening in the side of the surface of the elongated tube, the first opening capable of introducing fluid into the tissue where the vein has been extracted;

the proximal end of the elongated member coupled to a connector having two separate tubes communicating with the respective first and second lumens for the injection and removal of fluid from the tissue where the vein has been removed; and a stripper head detachably coupled to the elongated member.

41. The surgical apparatus of claim 40 wherein the vein is turned inside during extraction.

42. The surgical apparatus of claim 40 wherein the fluid is pressurized above 200 mmHG.

* * * * *